United States Patent [19]

Oviatt, Jr. et al.

[11] Patent Number: 4,746,751

[45] Date of Patent: May 24, 1988

[54] SILICONE REACTIVE/FLUORESCENT SILANE DYE COMPOSITIONS

[75] Inventors: Henry W. Oviatt, Jr.; Cary J. Reich, both of Laguna Hills, Calif.

[73] Assignee: Baxter Travenol Laboratories, Inc., Deerfield, Ill.

[21] Appl. No.: 47,690

[22] Filed: May 7, 1987

[51] Int. Cl.$^4$ .............................. C07F 7/08; C07F 7/18
[52] U.S. Cl. ................................... 556/456; 556/435; 556/442; 556/489; 8/506; 8/581
[58] Field of Search .................. 556/435, 413, 442

[56] References Cited

U.S. PATENT DOCUMENTS 3,647,740  3/1972  Loree .................. 260/37 SB
4,129,585  12/1978  Buder .................. 260/448.8 R Primary Examiner—Prince E. Willis
Assistant Examiner—Isabelle Rodriguez
Attorney, Agent, or Firm—Perman & Green

[57] ABSTRACT

The preparation of particular fluorescent silane dye compositions is disclosed. These silane dye compositions have particular utility as reactants in the preparation of silicone polymeric fluorescent dyes which can be ideally used as chemical indicators in biological sensors.

12 Claims, No Drawings

SILICONE REACTIVE/FLUORESCENT SILANE DYE COMPOSITIONS

BACKGROUND OF THE INVENTION

The present invention relates to the preparation of silicone compositions having photoactive dyes covalently bonded thereto. In particular, the present invention is directed to specific silicone polymer functional silane dye compounds in which the dye is present in non-diffusible and hydrolytically stable form, thereby rendering these compounds particularly useful in the preparation of in-vitro and in-vivo biological indicator systems.

The use of glass or plastic fibers a fraction of a millimeter in diameter for in vivo biomedical measurements, is a relatively new and important endeavor. Fiber-optic sensors can be as small as electrosensors and offer several distinct advantages. They are safe, involving no electrical connection to the body; the optical leads, very small and flexible, can be included in catheters for multiple sensing; and materials suitable for long term body implantation such as plastics, may be used.

The mechanism of fiber-optic sensor operation is relatively simple. Light from a suitable source travels along an optically conducting fiber to a receptor terminal where reflection, scattering or luminescence occurs. The light emanating from the sensing end of the fiber may be reflected by a tiny transducer that alternatively: (1) Varies the reflectance with some parameter of interest; (2) Back scatters the light due to elements in the medium into which the fiber is inserted; or (3) Absorbs the light, exciting some luminescent species, and returns emitted light of a longer wavelength at an intensity that varies with some component of the system in which the fiber is immersed. The affected light is then returned to a light measurement instrument which interprets the returned signal. Of these three general types of in-vivo fiber-optic sensing mechanisms, the luminescence technique has been recently developed as a measurement to determine the amounts of gasses in blood.

Peterson et al in U.S. Pat. No. 4,200,110 developed a pH sensor as an in vivo device for determination of acidity of the blood. The pH sensor is based on classical acid-based dye indicator chemistry, with a miniature spectrophotometric cell at the end of a pair of optic fibers. In the cell, the dye indicator is covalently bonded to polyacrylamide microspheres so that the terminal is non diffusible, and the sensor reusable. The dye-acrylic polymer composition offers a dye which is present in non-diffusible form but the hydrophilic polymer must be used in the form of gas permeable microspheres in order to function as the spectrophotometric cell of an optic fiber sensor.

The presence of unusually high or low oxygen content in blood samples may indicate various abnormalities. Peterson et al in U.S. Pat. No. 4,476,870 developed an optical sensor for measuring oxygen partial pressure, $PO_2$. The device is based on the quenching of the fluorescence of certain dyes by oxygen gas. Dyes are chosen for visible light excitation and are distributed on an adsorptive support medium for use as the light scattering terminal for the ingress and egress of optical fiber waves. Generally, a inorgasic gas adsorbant, such as silica gel, is used in the dye support medium. However, it has been found that such adsorbant materials are humidity-sensitive, thereby seriously interfering with fluorescence at high humidity.

Because of the importance of fiber-optic gas detecting chemical sensors, a need exists to develop or find materials which can act as molecular support mediums for those dyes which can be used effectively and efficiently in the indicator portions of fiber optic sensors. It has been found that chemically attaching dyes to certain silane compounds provides photoactive center materials which readily react with gas permeable silicone polymers to form non diffusable dye indicator compositions.

OBJECTS OF THE INVENTION

It is therefore an object of this invention to provide novel silane fluorescent dye compositions which are highly reactive with silicone polymers.

It is a further object of the present invention to provide silicone polymer compositions having the novel silane fluorescent dyes covalently bonded to the polymer backbone.

It is a still further object of this invention to provide a method for preparing novel silane dyes containing a fluorescent nucleus and functional groups reactive with certain silicone polymers.

It is yet still another object of this invention to provide silicone fluorescent dye polymers for use as a chemical indicator in fiber-optic sensor devices.

SUMMARY OF THE INVENTION

In accordance with the present invention, there is provided vinyl silane dyes and derivatives thereof having particular compatibility and reactivity with silicone polymer compositions to facilitate the preparation of non-diffusible polymer dye compositions. The novel vinyl silane dyes of the present invention are prepared by reacting a functionally substituted fluorescent dye with a vinyl silane compound. Derivative silane dyes are prepared by reacting the vinyl silane dyes with hydride functional silanes.

By the present invention there is provided silane dyes containing a fluorescent nucleus and a silicone polymer reactive moiety selected from the group of vinyl, alkoxy, acyloxy, and amide functional radicals. The vinyl functional silane dyes can be reacted with room temperature vulcanizable, hydride functional silicone elastomers to form non-diffusible silicone polymer dyes by a hydride addition reaction. Alternatively, the instant vinyl silane dyes can be reacted with other hydride functional silanes containing alkoxy, acyloxy, or amide groups to form compounds reactive with certain silicone polymers in condensation type reactions. The silane dye compounds of the present invention enable the expeditious preparation of dye containing gas permeable polymer compositions which can be used as unitary non-diffusible indicator elements in fiber optic biological probes.

DETAILED DESCRIPTION OF THE INVENTION

The fluorescent dye containing silane compounds of the invention are represented by the general formula:

$$Q-Z-\underset{R}{\overset{R}{\underset{|}{Si}}}-G \quad (I)$$

where G is an unsaturated radical such as vinyl, allyl, methallyl, or butenyl or a radical of the formula $$-\left(\underset{R}{\overset{R}{\underset{|}{C}}}\right)_n-\underset{V_3}{\overset{V_1}{\underset{|}{Si}}}-V_2 \quad (II)$$

where Q is a fluorescent dye; Z is a $C_{1-30}$ hydrocarbon radical; R is a hydrogen atom or a $C_{1-12}$ hydrocarbon radical; n is a whole number of from 1 to 50 and V1, V2 and V3 are independently a silicone polymer reactive substituent selected from the class of acyloxy, alkoxy, or amine radicals.

As indicated, Q is a fluorescent radical and may be any fluoresent moiety that satisfies the ultimate use of the present compositions as indicators in biological optical fiber probes. Therefore, Q may be any fluorescent moiety selected from the group of polycylic, homocyclic or heterocyclic aromatic hydrocarbons which demonstrate fluorescence or the extinction of fluorescence upon a chemical event, eq. the influence of molecular oxygen. Within the purview of the present invention preferred dyes are the polynuclear aromatic hydrocarbons particularly those of the pyrene, perylene, and benzoperylene family of dyes, having the following structural formulas:

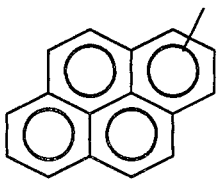
(III)

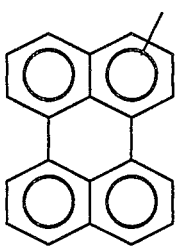
(IV)

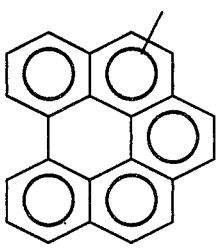
(V)

The fluorescent dye-silane compositions of the present invention can be conveniently prepared by reacting a substituted polynuclear aromatic fluorescent dye of the formula:

$$Q-Z-M \quad (VI)$$

wherein Q and Z are as defined above, and M is any silane reactive substituent such as halogen, hydroxyl, carboxyl, amine and amide radicals;

with an unsaturated organo functional silane having the formula:

$$X-\underset{R}{\overset{R}{\underset{|}{Si}}}-A \quad (VII)$$

where X is selected from the group of hydrogen, hydroxyl, and halogen radicals, R is as defined above, and A represents an alkenyl group selected from the class of vinyl, allyl, methallyl, or butenyl radicals. The composition prepared is represented by the following formula $$Q-Z-\underset{R}{\overset{R}{\underset{|}{Si}}}-A \quad (VIII)$$

This composition conforms to Formula I where G is an unsaturated organic radical.

To obtain the silane compositions conforming to formula II requires reaction of the compounds of formula VIII with hydride functional silane compounds represented by $$H-\underset{V_3}{\overset{V_1}{\underset{|}{Si}}}-V_2$$

Where V1 V2 and V3 are as defined above. An addition reaction takes place between the hydride radical of the silane and the unsaturated portion of A of formula VIII resulting in the compounds repesented in Formula II.

In one embodiment of the present invention vinyl dimethylchlorosilane having the formula $$Cl-\underset{CH_3}{\overset{CH_3}{\underset{|}{Si}}}-CH=CH_2 \quad (IX)$$

is reacted under Grignard conditions with an alkyl halide substituted polynuclear aromatic fluorescent compound such as 1-chloromethyl pyrene having the structural formula

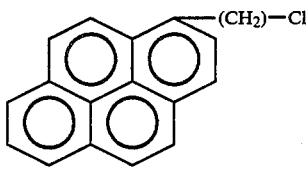
(X)

The reaction yields methyl(1-pyrenyl)dimethylvinyl silane of the structural formula

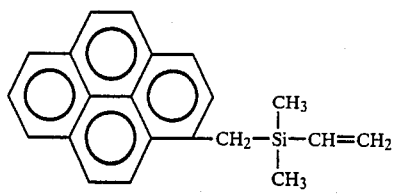
(XI)

This compound conforms to the structure of formula I wherein G of that formula is the vinyl group illustrated in the above compound (formula XI). This vinyl substituted fluorescent dye silane can be reacted with any addition cure type polymer to form a silicone polymeric dye having gas permeability which is useful as a fluorescent indicator element in biological sensors. For example, the vinyl functional silane dye (formula XI) can be bound covalently in an appropriate room temperature vulcanizable silicone elastomer by means of a hydride—vinyl addition cure. The reactivity of the vinyl group renders this compound an ideal candidate to covalently react with hydride functional room temperature vulcanizable silicone elastomers.

Because of the high reactivity of the vinyl group of the compound of formula XI, it can be further readily reacted with other addition cure type silane compounds to form further silicone polymer reactive compounds. As one example the methyl(1-pyrenyl)dimethylvinyl silane of formula XI can be reacted with triethoxy silane of the structural formula

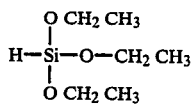

to form isomers of the structural formulas

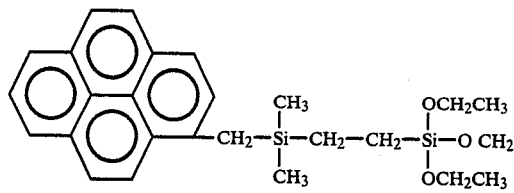

Methyl(1-Pyrenyl)dimethylethyl(2-triethylsiloxy)silane and

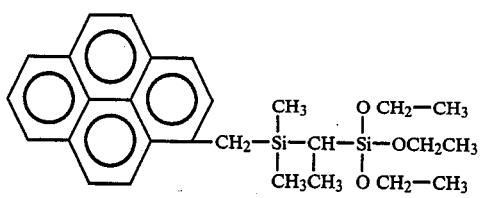

methyl(1-pyrenyl)dimethylethyl(1-triethylsiloxy)silane.

The isomers result from the optional addition of the hydride functional silane to either carbon atom of the vinyl group on the vinyl functional silane reactant. Both isomers of this compound conform to the structure of formulas I and II and, in this case, it is an alkoxy functional silane which is highly reactive and curable with appropriate alkoxy reactive silicone room temperature vulcanizable elastomers, particularly hydroxyl substituted polysiloxanes. By reaction with such silicone elastomers, another curable means of covalently bonding fluorescent dyes to a silicone polymer backbone is achieved.

This particular embodiment is merely one example of the novel dye substituted, silicone polymer reactive silanes of the present invention. Within the spirit and scope of the present invention, $V_1$, $V_2$ and $V_3$ may be any suitable functional groups which are hydrolyzable or condensation displaceable and hence can react with functional groups on silicone polymer backbones to form the instant silicone polymeric dyes. As a further illustration, the V groups of formula II may be acyloxy functional by using triacyloxy silane instead of the triethoxy silane of formula XII. Perferably, the V1, V2 and V3 groups are independently selected from silicone polymer reactive functional groups consisting of acyloxy, alkoxy or amine radicals.

The pyrene, perylene and benzoperylene polynuclear aromatic fluorescent dyes illustrated in formulas III, IV, and V are oxygen quenching materials. However any dyes may be used within the spirit and scope of the present invention. In the bivalent side chain shown in formula VI dyes, Z can be any hydrocarbon of up to 30 carbon atoms. Illustrative polynuclear dye reactants include the halogenated, hydroxyl and carboxylic acid derivatives of pyrene, perylene and benzoperylene. While any silane reactive functional group on the dye is operable within the purview of the present invention, it is preferrable to employ non oxygenated functional groups such as halogen, e.g., 1-chloromethylpyrene.

The method of the present invention is performed by techniques typically used with silane compounds. In the embodiment recited above, the halogenated aliphatic substituted polynuclear aromatic fluorescent dye is reacted with the vinyl functional halogenated silane in a typical Grignard Reaction with appropriate catalysts and solvents. The substitution takes place and the fluorescent dye-substituted silane is recovered.

The silane-dye compounds of this invention are useful in a variety of applications for which dyes are conventionally employed. However, as discussed above, a particularly preferred and desired use for these compounds is as reactants with siloxane homopolymers and co-polymers to form dye substituted polysiloxanes. These polymers are gas permeable and can be ideally used in the indicator portion of fiber-optic chemical sensors, especially fiber-optic $PO_2$ probes as described in U.S. Pat. No. 4,476,870 to Peterson.

The dye substituted silane compounds of the present invention have particular utility because of their reactivity with vulcanizable silicone systems. Consequently the addition of the instant dye compounds to one or two part elastomeric silicone compositions results in a dye substituted elastomer. The silane dyes can be added to a curable silicone elastomer and then applied to the terminals of a pair of optically active fibers to readily cure. The fluorescent tipped fiber can then be used as a solid gas permeable integral indicator medium for a biological sensor probe.

While not to be construed as limiting, it is believed that the reactivity of the present compounds with any particular silicone elastomer is due to the selection of a silicone polymer reactive substituent in the silane dye molecule. As an example, if the silane dye compound reacted with a polysiloxane elastomer within the purview of the present invention were an acyloxy functional silane of formula II, such an acyloxy group would react readily with hydroxyl groups on a silanol terminated siloxane polymer thereby covalently bonding the silane dye directly to the siloxane polymer backbone. This is illustrated as follows for a silicone polymer reactive carboxylate group.

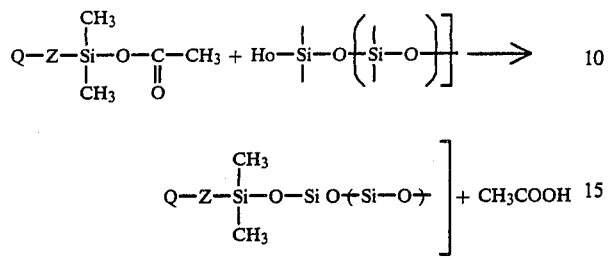

The following examples are included for further understanding of the invention. It should be understood that these examples are in now way intended to limit the scope of the present invention.

EXAMPLE I 34.1 grams of chloromethylpyrene was dissolved in methylene chloride and dried over anhydrous calcium chloride and magnesium sulfate to remove residual hydroxymethylpyrene or water. The chloromethylpyrene was filtered and the solvent removed by vacuum. The chloromethylpyrene was then redissolved in anhydrous tetrahydrofuran.

7.35 grams magnesium filings were placed in a 500 ml, 3 neck, round bottom flask fitted with a nitrogen purge on top of a water condenser and an addition funnel. The third port on the flask was capped with a rubber septa. The apparatus was purged with nitrogen for about >5 minutes, followed by flaming of the apparatus with a butane torch. After cooling to room temperature, the chloromethylpyrene solution in THF was added to the addition funnel by means of a syringe. 13 mls of 1,2-dibromoethane was also added to the addition funnel. 18.3 grams of vinyldimethylchlorosilane was then added to the flask. As addition of the contents of the addition funnel to the flask commenced, the contents of the flask began to reflux. Refluxing was continued until the addition was complete. The flask was then heated for an additional 2 hours by means of a water bath.

When the heating was terminated and the reaction allowed to cool, a precipitate formed. The reaction mixture was allowed to settle and a solid precipitate was recovered by vacuum filtering. The precipitate was washed with hexane, and the solvent collected and evaporated on a rotary evaporator. The resulting viscous liquid was then fractionally distilled under vacuum. The viscous, green fluorescent liquid that subsequently crystallized was identified as methyl(1-pyrenyl)dimethylvinylsilane.

EXAMPLE II

The following illustrates the use of the vinyl functional silane dye adduct of Example I in one-part room temperature vulcanizable silicone systems and the preparation of a fluorescent indicator element on the terminal of an optical fiber.

The fluorescent vinyl functional silane dye prepared in Example I is blended into a two part addition cured silicone elastomer containing active hydride centers. When the blend was cured it was found the the vinyl group of the dye/silane compound had reacted with the hydride radicals group of the silicone elastomer to complete a vinyl addition and form a dye containing silicone polymer.

When a fiber optical probe was dipped into the curable blend and allowed to cure a gas permeable integral indicator terminal was formed for the probe strand. The optically active probe was subjected to a favorable leachability test which indicated the covalent chemical bonding of the fluorescent pyrene molecule to the silicone polymer.

EXAMPLE III

To a 100 ml round bottom flask was added 2.0 grams methyl(1-pyrenyl)dimethylvinylsilane followed by 5 milligrams $H_2P_tCl_6$ (hexachloroplatinic acid) in isopropyl alcohol. The isopropyl alcohol was then removed under vacuum. Then 4 mls of triethoxysilane was added to the flask and the contents refluxed for 2 hours. After cooling the reaction was decolorized with Norit and the product chromatographed on silica gel, using a gradient elution starting with hexane and ending with chloroform. The isolated isomeric products were then distilled separately on a micromolecular still to yield both isomers of the alkoxy functional silane dye, methyl(-pyrenyl)dimethylethyl(triethylsiloxy)silane, the formulas of which were indicated above.

EXAMPLE IV

The following illustrates the use of the alkoxyfunctional dye-silane adduct of Example III in a one part room temperature vulcanizable silicone system. The alkoxy functional/fluorescent dye silane adduct prepared in Example III is blended into a two part room temperature vulcanizable elastomer comprising silanol terminated polydimethylsiloxane as the matrix backbone, triethoxysilane as the crosslinker and tin octoate as the catalyst. Upon curing there results a crosslinked branched polysiloxane in which the pyrene molecule is covalently chemically bonded to the silicone resin network. An optically active indicator element of this material can also be prepared in the same manner as in Example II.

Although variations are shown in the present application, many modifications and ramifications will occur to those skilled in the art upon a reading of the present disclosure. These, too, are intended to be included herein.

What is claimed:
1. A silane dye composition having the formula

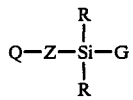

wherein Q is a fluorescent dye group; Z is a $C_{1-30}$ hydrocarbon radical; R is a hydrogen atom or a $C_{1-12}$ hydrocarbon radical; and G is a functional group capable of reacting with a silicone polymer functional group.

2. The composition of claim 1 wherein G is an unsaturated organic functional group selected from the class of vinyl, alkyl, methallyl, or butenyl radicals.

3. The composition of claim 1 wherein Q is a fluorescent dye selected from the group of polynuclear aromatic dyes composed of pyrene, perylene, benzopyrlene and derivatives thereof.

4. The dye composition of claim 1 wherein G is a radical of the formula $$-\left(\begin{array}{c} R \\ | \\ C \\ | \\ R \end{array}\right)_n \begin{array}{c} V_1 \\ | \\ -Si-V_2 \\ | \\ V_3 \end{array}$$

where R is a hydrogen atom or a $C_{1-12}$ hydrocarbon radical; n is a whole number of from 1 to 50; and $V_1$, $V_2$ and $V_3$ are independently a silicone polymer reactive substituent.

5. The composition of claim 4 wherein the $V_1$, $V_2$ and $V_3$ silicone polymer reactive groups are selected from the class of radicals consisting of alkoxy, acyloxy or amine groups.

6. The composition of claim 1 comprising methyl(pyrenyl)dimethylvinyl silane.

7. The composition of claim 5 comprising methyl(pyrenyl)dimethylethyl(triethylsiloxy)silane.

8. A method of preparing a dye-silane composition comprising reacting a substituted polynuclear aromatic hydrocarbon based fluorescent dye of the formula:

Q-Z-M wherein Q is a polynuclear aromatic fluorescent dye moiety, Z is a $C_{1-30}$ hydrocarbon radical, and M is a silane reactive substituent selected from the group consisting of halogen, hydroxyl, carboxyl, amine, and amide groups;

with an unsaturated organo functional silane having the formula:

$$\begin{array}{c} R \\ | \\ X-Si-A \\ | \\ R \end{array}$$

wherein X is selected from the group of hydrogen, hydroxyl, and halogen radicals; R is a hydrogen atom or a $C_{1-12}$ hydrocarbon radical and A is an alkenyl group to form the dye silane of the formula $$\begin{array}{c} R \\ | \\ Q-Z-Si-A \\ | \\ R \end{array}$$

9. The process of claim 8 wherein the resulting unsaturated organo silane dye is further reacted with a hydride functional silane of the formula:

$$\begin{array}{c} V_1 \\ | \\ H-Si-V_2 \\ | \\ V_3 \end{array}$$

in an addition reaction with the unsaturated A group to form $$Q-Z-\begin{array}{c} R \\ | \\ Si \\ | \\ R \end{array}-\left(\begin{array}{c} R \\ | \\ C \\ | \\ R \end{array}\right)_n \begin{array}{c} V_1 \\ | \\ -Si-V_2 \\ | \\ V_3 \end{array}$$

wherein n is a whole number from 1 to 50 and $V_1$ $V_2$ and $V_3$ are independently a silicone polymer reactive substituent selected from the class consisting of alkoxy, acyloxy and amine radicals.

10. The process of claim 8 wherein the alkenyl group A is selected from the group consisting of vinyl, allyl, methallyl, and butenyl radicals.

11. The process of claim 8 wherein the product formed is methyl(pyrenyl)dimethylvinyl silane.

12. The process of claim 9 wherein the product formed is methyl(pyrenyl)dimethylethyl(triethylsiloxy)silane.

* * * * *